US012805771B2

(12) United States Patent
Li et al.

(10) Patent No.: US 12,805,771 B2
(45) Date of Patent: Nov. 24, 2026

(54) BLOOD OXYGEN DETECTION METHOD AND APPARATUS

(71) Applicant: HUAWEI TECHNOLOGIES CO., LTD., Shenzhen (CN)

(72) Inventors: Yue Li, Beijing (CN); Yan Li, Shenzhen (CN); Bin Yang, Shenzhen (CN); Jing Li, Shenzhen (CN); Linfeng Zhou, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 857 days.

(21) Appl. No.: 17/434,822

(22) PCT Filed: Mar. 5, 2020

(86) PCT No.: PCT/CN2020/077946
§ 371 (c)(1),
(2) Date: Aug. 30, 2021

(87) PCT Pub. No.: WO2020/182047
PCT Pub. Date: Sep. 17, 2020

(65) Prior Publication Data

US 2022/0142529 A1 May 12, 2022

(30) Foreign Application Priority Data

Mar. 12, 2019 (CN) ......................... 201910186108.7

(51) Int. Cl.
*A61B 5/1455* (2006.01)
*A61B 5/00* (2006.01)

(52) U.S. Cl.
CPC .......... *A61B 5/14551* (2013.01); *A61B 5/681* (2013.01); *A61B 5/7214* (2013.01)

(58) Field of Classification Search
CPC ....... A61B 5/14551; A61B 5/681; A61B 5/72; A61B 5/7214
See application file for complete search history.

(56) References Cited

U.S. PATENT DOCUMENTS 7,469,157 B2 12/2008 Diab et al.
9,526,431 B2 * 12/2016 Zakharov ............... A61B 5/721
(Continued)

FOREIGN PATENT DOCUMENTS

CN 101940475 A 1/2011
CN 103169478 A 6/2013
(Continued)

*Primary Examiner* — Severo Antonio P Lopez
(74) *Attorney, Agent, or Firm* — Maier & Maier, PLLC

(57) ABSTRACT

A blood oxygen detection method, including: obtaining at least two red light signals, at least two infrared signals, and a green light signal; determining red light direct current data and a component signal of a red light alternating current signal based on the at least two red light signals; determining infrared direct current data and a component signal of an infrared alternating current signal based on the at least two infrared signals, where the component signal includes an arterial signal; determining red light alternating current data based on the component signal of the red light alternating current signal and the green light signal; determining infrared alternating current data based on the component signal of the infrared alternating current signal and the green light signal; and determining blood oxygen saturation based on the red light direct current data, the red light alternating current data, and the infrared direct current data.

14 Claims, 4 Drawing Sheets

(56) References Cited

U.S. PATENT DOCUMENTS

| | | | | |
|---|---|---|---|---|
| 10,568,525 | B1* | 2/2020 | Wu | A61B 5/6824 |
| 2015/0355604 | A1* | 12/2015 | Fraser | G01J 1/0437 368/10 |
| 2016/0367154 | A1 | 12/2016 | Gladshtein et al. | |
| 2018/0116607 | A1* | 5/2018 | Yu | A61B 5/681 |
| 2018/0303359 | A1* | 10/2018 | O'Brien | A61B 5/02427 |
| 2020/0345252 | A1* | 11/2020 | Huijbregts | A61B 5/02416 |

FOREIGN PATENT DOCUMENTS

| | | | |
|---|---|---|---|
| CN | 103417222 | A | 12/2013 |
| CN | 105249939 | A | 1/2016 |
| CN | 105866761 | A | 8/2016 |
| CN | 107432741 | A | 12/2017 |
| CN | 108420440 | A | 8/2018 |
| CN | 108652642 | A | 10/2018 |
| CN | 108937957 | A | 12/2018 |
| CN | 109044322 | A | 12/2018 |
| CN | 109549624 | A | 4/2019 |
| WO | 2016/015009 | A1 | 1/2016 |
| WO | 2017/133883 | A1 | 8/2017 |

* cited by examiner

BLOOD OXYGEN DETECTION METHOD AND APPARATUS

CROSS-REFERENCE TO RELATED APPLICATIONS

This application is a National Stage of International Application No. PCT/CN2020/077946, filed on Mar. 5, 2020, which claims priority to Chinese Patent Application No. 201910186108.7, filed on Mar. 12, 2019, both of which are hereby incorporated by reference in their entireties.

TECHNICAL FIELD

The embodiments relate to the field of blood oxygen detection, and in particular, to a wrist pulse blood oxygen detection method and apparatus based on multi-channel and independent component analysis.

BACKGROUND

Blood oxygen saturation (oxygen saturation, SpO2) is a concentration of blood oxygen in blood. The blood oxygen saturation is an important physiological parameter of respiratory circulation and describes an ability of the blood to carry and deliver oxygen. A metabolism process of a human body is a biological oxidation process, and oxygen required in the metabolism process enters the blood of the human body through a respiratory system. The oxygen entering the blood of the human body and deoxyhemoglobin (hemoglobin, Hb) in red blood cells are combined to form oxyhemoglobin HbO2, and then the oxyhemoglobin is delivered to cells of various parts of the human body. SpO2 is a percentage of HbO2 in the blood to a total hemoglobin capacity. In other words, SpO2=HbO2/(HbO2+Hb)×100%. Usually, the percentage is about 98%.

Currently, in some pulse blood oxygen detection, because blood vessels are sparsely distributed on a wrist, and on a surface layer, many veins are distributed and a pulse blood oxygen signal is relatively weak, interference caused by the veins cannot be ignored in data collected by using a single red light channel and an infrared light channel. Consequently, a signal-to-noise ratio of the data is relatively low. In addition, it is sensitive to a relative motion between skin and a sensor when one detection point is used for measurement. Therefore, this easily leads to interference caused by the motion.

SUMMARY

Embodiments provide a blood oxygen detection method and apparatus. Alternating current/direct current decomposition is performed on red light signals and infrared signals collected at a plurality of collection points, an alternating current part is separated into a plurality of independent components by using an independent component analysis algorithm, and then correlation is performed between each independent component and a green light signal. In this way, interference of venous blood flows and capillaries can be effectively eliminated, a disadvantage of a low signal-to-noise ratio is made up, and an accuracy of a blood oxygen measurement on a wrist is increased.

According to a first aspect, a blood oxygen detection method is provided, where the method includes: obtaining at least two red light signals, at least two infrared signals, and a green light signal; determining red light direct current data and a component signal of a red light alternating current signal based on the at least two red light signals; and determining infrared direct current data and a component signal of an infrared alternating current signal based on the at least two infrared signals, where the component signal includes an arterial signal; determining red light alternating current data based on the component signal of the red light alternating current signal and the green light signal; and determining infrared alternating current data based on the component signal of the infrared alternating current signal and the green light signal; and determining blood oxygen saturation based on the red light direct current data, the red light alternating current data, the infrared direct current data, and the infrared alternating current data.

In a possible implementation, the determining red light direct current data and a component signal of a red light alternating current signal based on the at least two red light signals; and determining infrared direct current data and a component signal of an infrared alternating current signal based on the at least two infrared signals includes: determining at least two red light direct current signals and at least two red light alternating current signals based on the at least two red light signals; determining the red light direct current data based on the at least two red light direct current signals; determining at least two infrared direct current signals and at least two infrared alternating current signals based on the at least two infrared signals; determining the infrared direct current data based on the at least two infrared direct current signals; and determining the component signal of the red light alternating current signal based on the at least two red light alternating current signals, and determining the component signal of the infrared alternating current signal based on the at least two infrared alternating current signals.

In a possible implementation, the determining the component signal of the red light alternating current signal based on the at least two red light alternating current signals, and determining the component signal of the infrared alternating current signal based on the at least two infrared alternating current signals includes: separating at least one component signal of the at least two red light alternating current signals by using an independent component analysis algorithm or a principal component analysis algorithm, to obtain at least one component signal of the red light alternating current signal, where the at least one component signal of the red light alternating current signal includes an arterial signal; and separating at least one component signal of the at least two infrared alternating current signals by using the independent component analysis algorithm or the principal component analysis algorithm, to obtain at least one component signal of the infrared alternating current signal, where the at least one component signal of the infrared alternating current signal includes an arterial signal.

In a possible implementation, the determining red light alternating current data based on the component signal of the red light alternating current signal and the green light signal; and determining infrared alternating current data based on the component signal of the infrared alternating current signal and the green light signal includes: performing filtering processing on the green light signal; and determining the red light alternating current data based on the component signal of the red light alternating current signal and a green light signal obtained after the filtering processing, and determining the infrared alternating current data based on the component signal of the infrared alternating current signal and the green light signal obtained after the filtering processing.

In a possible implementation, the determining red light alternating current data based on the component signal of the red light alternating current signal and the green light signal; and determining infrared alternating current data based on the component signal of the infrared alternating current signal and the green light signal includes: performing comparison based on the at least one component signal of the red light alternating current signal and the green light signal, and determining that data corresponding to at least one component signal, of the red light alternating current signal, closest to the green light signal is the red light alternating current data; and performing comparison based on the at least one component signal of the infrared alternating current signal and the green light signal, and determining that data corresponding to at least one component signal, of the infrared alternating current signal, closest to the green light signal is the infrared alternating current data.

In a possible implementation, the red light direct current data is an average value, a maximum value, a minimum value, or a median of the at least two red light direct current signals; and the infrared direct current data is an average value, a maximum value, a minimum value, or a median of the at least two infrared direct current signals.

In a possible implementation, the determining blood oxygen saturation based on the red light direct current data, the red light alternating current data, the infrared direct current data, and the infrared alternating current data includes: determining pulse blood oxygen based on the red light direct current data, the red light alternating current data, the infrared direct current data, and the infrared alternating current data; and querying a pre-configured comparison table based on the pulse blood oxygen, to determine the blood oxygen saturation.

According to a second aspect, a blood oxygen detection apparatus is provided, and the apparatus includes: at least two red light sensors, at least two infrared sensors, a green light sensor, and a processor. The at least two red light sensors are configured to obtain at least two red light signals, the at least two infrared sensors are configured to obtain at least two infrared signals, and the green light sensor is configured to obtain a green light signal. The processor is configured to: determine red light direct current data and a component signal of a red light alternating current signal based on the at least two red light signals; and determine infrared direct current data and a component signal of an infrared alternating current signal based on the at least two infrared signals. The component signal includes an arterial signal. The processor is further configured to: determine red light alternating current data based on the component signal of the red light alternating current signal and the green light signal; and determine infrared alternating current data based on the component signal of the infrared alternating current signal and the green light signal. The processor is further configured to determine blood oxygen saturation based on the red light direct current data, the red light alternating current data, the infrared direct current data, and the infrared alternating current data.

In a possible implementation, the processor is further configured to: determine at least two red light direct current signals and at least two red light alternating current signals based on the at least two red light signals; determine the red light direct current data based on the at least two red light direct current signals; determine at least two infrared direct current signals and at least two infrared alternating current signals based on the at least two infrared signals; determine the infrared direct current data based on the at least two infrared direct current signals; determine the component signal of the red light alternating current signal based on the at least two red light alternating current signals; and determine the component signal of the infrared alternating current signal based on the at least two infrared alternating current signals.

In a possible implementation, the processor is further configured to: separate at least one component signal of the at least two red light alternating current signals by using an independent component analysis algorithm or a principal component analysis algorithm, to obtain at least one component signal of the red light alternating current signal, where the at least one component signal of the red light alternating current signal includes an arterial signal; and separate at least one component signal of the at least two infrared alternating current signals by using the independent component analysis algorithm or the principal component analysis algorithm, to obtain at least one component signal of the infrared alternating current signal, where the at least one component signal of the infrared alternating current signal includes an arterial signal.

In a possible implementation, the processor is further configured to: perform filtering processing on the green light signal; determine the red light alternating current data based on the component signal of the red light alternating current signal and a green light signal obtained after the filtering processing; and determine the infrared alternating current data based on the component signal of the infrared alternating current signal and the green light signal obtained after the filtering processing.

In a possible implementation, the processor is further configured to: perform comparison based on the at least one component signal of the red light alternating current signal and the green light signal, and determine that data corresponding to at least one component signal, of the red light alternating current signal, closest to the green light signal is the red light alternating current data; and perform comparison based on the at least one component signal of the infrared alternating current signal and the green light signal, and determine that data corresponding to at least one component signal, of the infrared alternating current signal, closest to the green light signal is the infrared alternating current data.

In a possible implementation, the red light direct current data is an average value, a maximum value, a minimum value, or a median of the at least two red light direct current signals. The infrared direct current data is an average value, a maximum value, a minimum value, or a median of the at least two infrared direct current signals.

In a possible implementation, the processor is further configured to: determine pulse blood oxygen based on the red light direct current data, the red light alternating current data, the infrared direct current data, and the infrared alternating current data; and query a pre-configured comparison table based on the pulse blood oxygen, to determine the blood oxygen saturation.

In a possible implementation, the apparatus is a wearable intelligent device, and includes a watchband and an intelligent wearable device body. At least one red light sensor and at least one infrared sensor are disposed on the watchband. At least one red light sensor, at least one infrared sensor, and a processor are disposed on the intelligent wearable device body. A green light sensor is disposed on the watchband or the intelligent wearable device body.

According to a third aspect, a blood oxygen detection apparatus is provided, where the apparatus includes: a collection module, configured to obtain at least two red light signals, at least two infrared signals, and a green light signal; an alternating current/direct current decomposition module, configured to: determine red light direct current data and a component signal of a red light alternating current signal based on the at least two red light signals, and determine infrared direct current data and a component signal of an infrared alternating current signal based on the at least two infrared signals, where the component signal includes an arterial signal; a component analysis module, configured to: determine red light alternating current data based on the component signal of the red light alternating current signal and the green light signal, and determine infrared alternating current data based on the component signal of the infrared alternating current signal and the green light signal; and a blood oxygen conversion module, configured to determine blood oxygen saturation based on the red light direct current data, the red light alternating current data, the infrared direct current data, and the infrared alternating current data.

In a possible implementation, the alternating current/direct current decomposition module is further configured to: determine at least two red light direct current signals and at least two red light alternating current signals based on the at least two red light signals; determine the red light direct current data based on the at least two red light direct current signals; determine at least two infrared direct current signals and at least two infrared alternating current signals based on the at least two infrared signals; determine the infrared direct current data based on the at least two infrared direct current signals; determine the component signal of the red light alternating current signal based on the at least two red light alternating current signals; and determine the component signal of the infrared alternating current signal based on the at least two infrared alternating current signals.

In a possible implementation, the component analysis module is further configured to: separate at least one component signal of the at least two red light alternating current signals by using an independent component analysis algorithm or a principal component analysis algorithm, to obtain at least one component signal of the red light alternating current signal, where the at least one component signal of the red light alternating current signal includes an arterial signal; and separate at least one component signal of the at least two infrared alternating current signals by using the independent component analysis algorithm or the principal component analysis algorithm, to obtain at least one component signal of the infrared alternating current signal, where the at least one component signal of the infrared alternating current signal includes an arterial signal.

In a possible implementation, the apparatus further includes a preprocessing module. The preprocessing module is configured to perform filtering processing on the green light signal. The component analysis module is further configured to: determine the red light alternating current data based on the component signal of the red light alternating current signal and a green light signal obtained after the filtering processing; and determine the infrared alternating current data based on the component signal of the infrared alternating current signal and the green light signal obtained after the filtering processing.

In a possible implementation, the component analysis module is further configured to: perform comparison based on the at least one component signal of the red light alternating current signal and the green light signal, and determine that data corresponding to at least one component signal, of the red light alternating current signal, closest to the green light signal is the red light alternating current data; and perform comparison based on the at least one component signal of the infrared alternating current signal and the green light signal, and determine that data corresponding to at least one component signal, of the infrared alternating current signal, closest to the green light signal is the infrared alternating current data.

In a possible implementation, the red light direct current data is an average value, a maximum value, a minimum value, or a median of the at least two red light direct current signals; and the infrared direct current data is an average value, a maximum value, a minimum value, or a median of the at least two infrared direct current signals.

In a possible implementation, the blood oxygen conversion module is further configured to: determine pulse blood oxygen based on the red light direct current data, the red light alternating current data, the infrared direct current data, and the infrared alternating current data; and query a pre-configured comparison table based on the pulse blood oxygen, to determine the blood oxygen saturation.

According to a fourth aspect, a computer-readable storage medium storing a program is provided. The program includes instructions, and when the instructions are executed by a computer, the computer is enabled to perform the method according to the first aspect.

According to a fifth aspect, a computer program product including instructions is provided, and when the computer program product runs, the method according to the first aspect is performed.

The embodiments provide a blood oxygen detection method and apparatus. More information is collected by using a plurality of measurement points, collected alternating current information is separated by using an independent component algorithm, and denoising is performed by using a green light signal, so that interference caused by venous blood flows, capillaries, and the like can be eliminated, a disadvantage of a low signal-to-noise ratio is made up, and accuracy of blood oxygen measurement on a wrist is increased.

DETAILED DESCRIPTION OF THE EMBODIMENTS

The following describes the solutions in the embodiments with reference to the accompanying drawings.

The embodiments are applied to wrist blood oxygen detection. Hemoglobin has different absorption rates for red light and infrared light. HbO2 absorbs more near-infrared light (infrared radiation, IR), and a wavelength of the IR is usually about 900 nm. Hb absorbs more red light, and a wavelength of the red light is usually about 600 nm. The red light and the infrared light are radiated into human tissue at the same time. Because blood flows of veins and other body tissue are relatively constant, absorption of light can be approximately considered as a fixed value. Arteries periodically expand with a pulse, and therefore a total blood volume per unit volume changes periodically. Therefore, absorption of the red light and infrared light by the arteries changes periodically with the pulse.

Figure 1A:
FIG. 1*a* is a schematic diagram of a pulse blood oxygen meter according to the conventional technology.
Figure 1B:
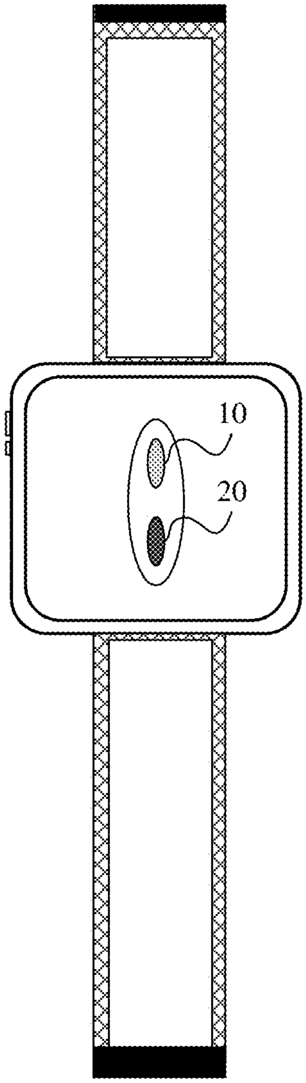
FIG. 1*b* is a schematic diagram of another pulse blood oxygen meter according to the conventional technology.

Some existing blood oxygen detection apparatuses use a finger clip type, and a finger of a measured person is put into a pulse oximeter of a finger clip type for measurement. As shown in FIG. 1*a*, in this solution, because the finger of the measured person needs to be clipped by the oximeter, the oximeter seriously interferes with a movement of the finger. In addition, it is more likely to cause discomfort when the finger is clipped for a long time. There are also some blood oxygen detection apparatuses using wrist-type single-channel measurement. A single-channel means that a signal is collected by using a single detection point. As shown in FIG. 1*b*, 10 is a red light sensor, and 20 is an infrared sensor. Pulse blood oxygen is detected by wearing the oximeter on the wrist. However, because blood vessels are sparsely distributed on the wrist and many veins are distributed on a surface layer, a pulse blood oxygen signal is relatively weak. Interference caused by the veins cannot be ignored in data collected by a single red light and infrared sensor. Consequently, a signal-to-noise ratio of the data is relatively low. In addition, it is sensitive to a relative motion between skin and a sensor when a single detection point is used for measurement. Therefore, this easily leads to interference caused by the motion.

To resolve the problem in the foregoing technology, in a detection method, information about a plurality of detected parts is collected, and collected red light and infrared signals are divided into a red light alternating current signal, an infrared alternating current signal, a red light direct current signal, and an infrared direct current signal. Because signals collected by the sensor are a large quantity of original signals, data that can best reflect a current blood oxygen status needs to be extracted from the collected original signals. Therefore, in the embodiments, red light alternating current data and infrared alternating current data are determined from the red light alternating current signal and the infrared alternating current signal through a correlation analysis with a green light signal. In addition, red light direct current data and infrared direct current data are determined by using the red light direct current signal and the infrared direct current signal. The red light direct current data in the embodiments may be an average value, a maximum value, a minimum value, a median, or the like of a plurality of red light direct current signals. The infrared direct current data in the embodiments may be an average value, a maximum value, a minimum value, a median, or the like of a plurality of infrared direct current signals. A green light signal is used to perform denoising on the red light alternating current data and the infrared alternating current data, so that interference caused by venous blood flows, capillaries, and the like can be eliminated. Finally, red light alternating current data, infrared alternating current data, red light direct current data, and infrared direct current data that are obtained after the denoising are used to calculate blood oxygen saturation. A disadvantage of a low signal-to-noise ratio is made up and accuracy of a blood oxygen measurement on the wrist is increased.

The following describes the solutions in the embodiments with reference to the accompanying drawings.

Figure 2:
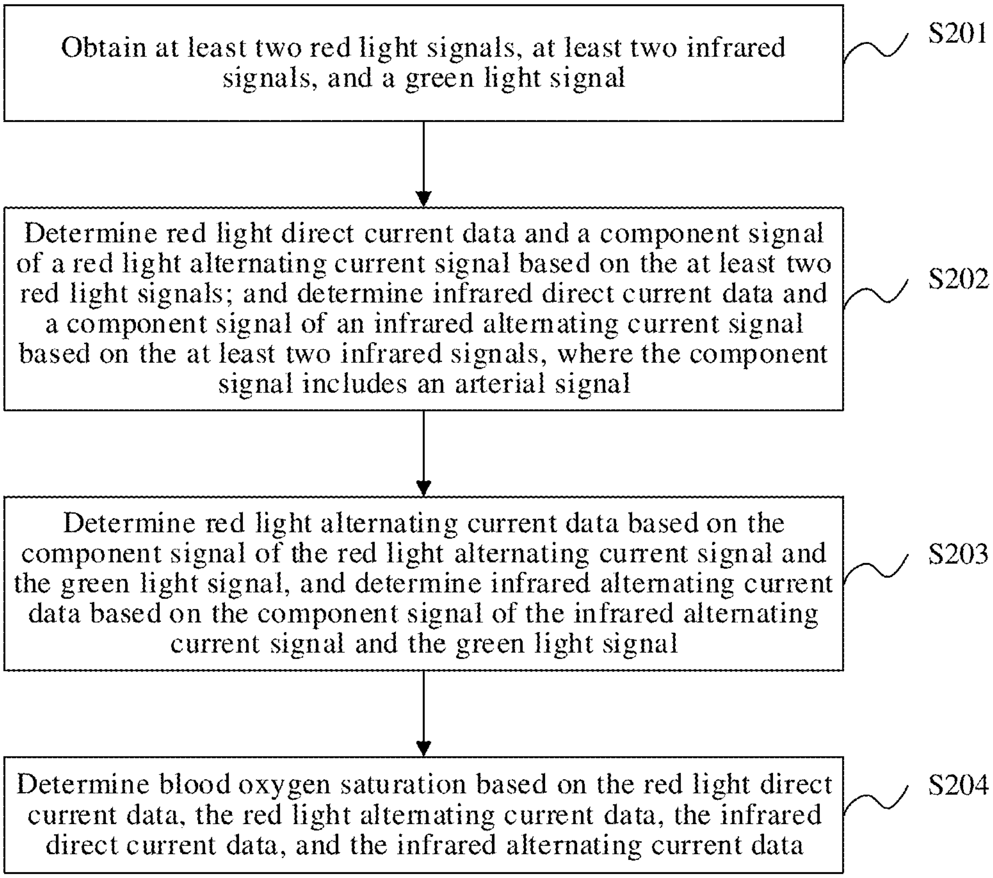
FIG. 2 is a flowchart of a blood oxygen detection method according to an embodiment.

FIG. 2 is a flowchart of a blood oxygen detection method according to an embodiment. As shown in FIG. 2, the method includes the following steps.

S201: Obtain at least two red light signals, at least two infrared signals, and a green light signal.

A signal of a measured user is collected by using at least two red light sensors, at least two infrared sensors, and a green light sensor. In an example, one detection point may include one red light sensor and one infrared sensor. In an embodiment, two detection points may be included, and each detection point obtains one red light signal and one infrared signal. In addition, a green light detection point is further included, and is configured to obtain a green light signal.

S202: Determine red light direct current data and a component signal of a red light alternating current signal based on the at least two red light signals; and determine infrared direct current data and a component signal of an infrared alternating current signal based on the at least two infrared signals, where the component signal includes an arterial signal.

Alternating current/direct current separation is performed on the at least two collected red light signals, to obtain the red light direct current data and the component signal of the red light alternating current signal. In addition, alternating current/direct current decomposition is performed on the at least two collected infrared signals, to obtain the infrared direct current data and the component signal of the infrared alternating current signal. In an example, the component signal includes the arterial signal. In another example, the component signal may alternatively include a capillary signal, another noise signal, or the like.

S203: Determine red light alternating current data based on the component signal of the red light alternating current signal and the green light signal, and determine infrared alternating current data based on the component signal of the infrared alternating current signal and the green light signal.

Compared with red light, green light can be absorbed by oxyhemoglobin and deoxyhemoglobin, a signal obtained by using the green light as a light source is better, and a signal-to-noise ratio is also better than that of another light source. Therefore, in the embodiments, the green light is used for measurement, and is used as reference data of a pulse signal. In an example, there are a plurality of component signals, including a pulse signal. The green light signal is used to select the pulse signal from the plurality of component signals as alternating current data, so as to determine the red light alternating current data and the infrared alternating current data.

S204: Determine blood oxygen saturation based on the red light direct current data, the red light alternating current data, the infrared direct current data, and the infrared alternating current data.

In the embodiments, more information is collected by using a plurality of measurement points, then collected alternating current information is separated by using an independent component analysis algorithm, and denoising is performed by using the green light signal, so that interference caused by venous blood flows, capillaries, and the like can be eliminated, a disadvantage of a low signal-to-noise ratio is made up, and accuracy of a blood oxygen measurement on a wrist is increased.

Figure 3:
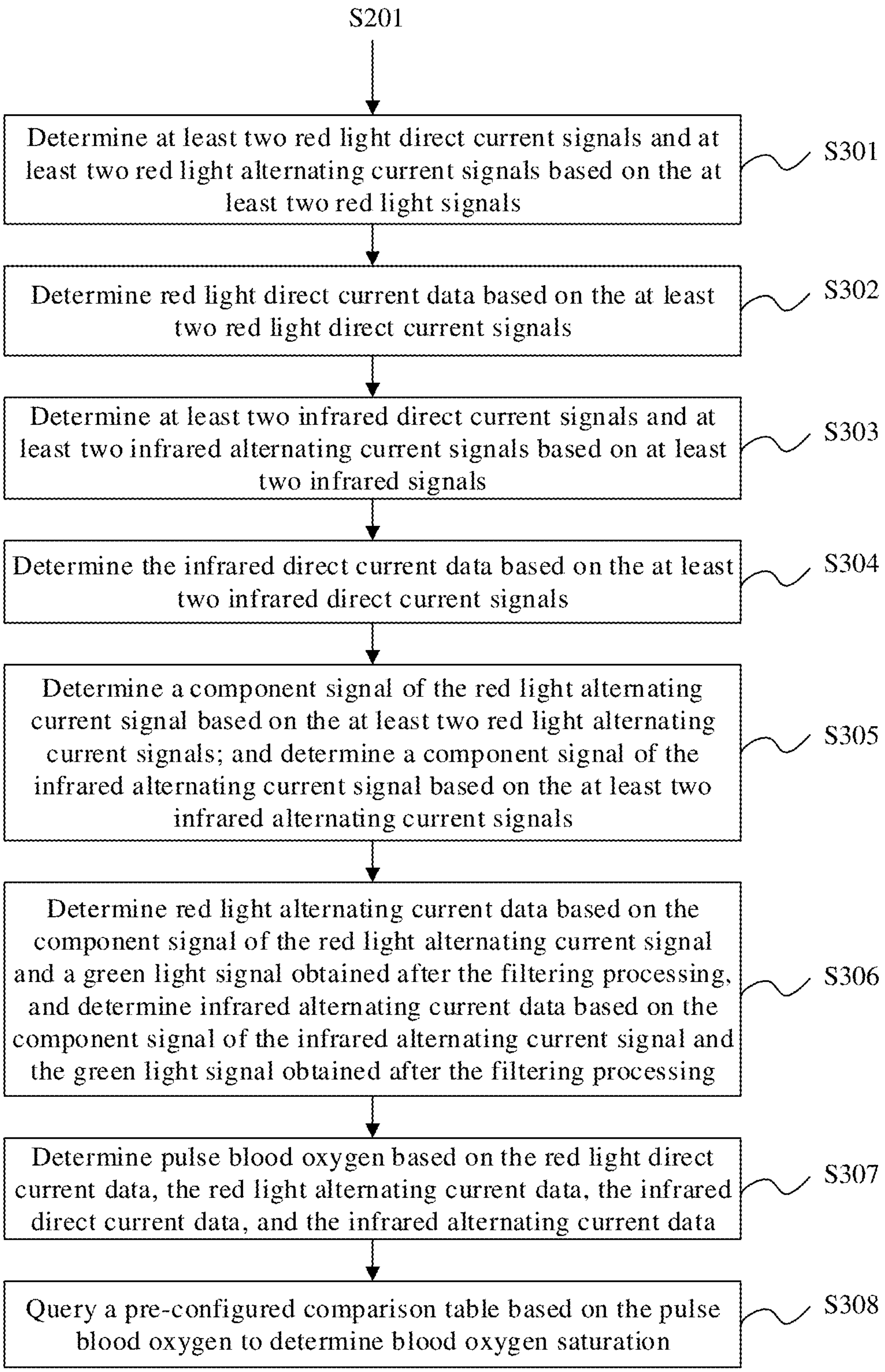
FIG. 3 is a flowchart of another blood oxygen detection method according to an embodiment.

The following further describes the solutions of the embodiments. FIG. 3 is a flowchart of another blood oxygen detection method according to an embodiment.

As shown in FIG. 3, after S201, the method further includes the following steps.

S301: Determine at least two red light direct current signals and at least two red light alternating current signals based on the at least two red light signals.

Alternating current/direct current separation is performed on red light signals received by a plurality of detection points, to obtain a plurality of red light direct current signals and a plurality of red light alternating current signals. In an example, alternating current/direct current separation is performed on a red light signal received at each detection point, and a red light direct current signal and a red light alternating current signal are obtained at each detection point. In another example, detection may be further performed on each detection point a plurality of times. In each time of detection, alternating current/direct current separation is performed on a red light signal received at each detection point, and a red light direct current signal and a red light alternating current signal are obtained at each detection point.

S302: Determine red light direct current data based on the at least two red light direct current signals.

In an example, one piece of red light direct current data is determined based on a plurality of red light direct current signals determined by a plurality of detection points. In another example, one piece of red light direct current data may be determined based on a plurality of red light direct current signals determined through a plurality of times of measurement at each detection point. The red light direct current data may be an average value, a maximum value, a minimum value, a median, or the like of the plurality of red light direct current signals. A person of ordinary skill in the art should note that the direct current data reflects a status of deoxyhemoglobin in a venous blood vessel. Because a blood flow in the venous blood vessel is relatively constant, a plurality of direct current signals may be combined into the red light direct current data, and any equivalent variation or replacement shall fall within the scope of the embodiments.

S303: Determine at least two infrared direct current signals and at least two infrared alternating current signals based on the at least two infrared signals.

Alternating current/direct current separation is performed on infrared signals received by a plurality of detection points, to obtain a plurality of infrared direct current signals and a plurality of infrared alternating current signals. In an example, alternating current/direct current separation is performed on an infrared signal received at each detection point, and an infrared direct current signal and an infrared alternating current signal are obtained at each detection point. In another example, detection may be performed on each detection point a plurality of times. In each time of detection, alternating current/direct current separation is performed on an infrared signal received at each detection point, and an infrared direct current signal and an infrared alternating current signal are obtained at each detection point.

S304: Determine the infrared direct current data based on the at least two infrared direct current signals.

In an example, one piece of infrared direct current data is determined based on a plurality of infrared direct current signals determined by a plurality of detection points. In another example, one piece of infrared direct current data may be determined based on a plurality of infrared direct current signals determined through a plurality of times of measurement at each detection point. The infrared direct current data may be an average value, a maximum value, a minimum value, a median, or the like of the plurality of infrared direct current signals. A person of ordinary skill in the art should note that the direct current data reflects a status of oxyhemoglobin in a venous blood vessel. Because a blood flow in the venous blood vessel is relatively constant, a plurality of direct current signals may be combined into the red light direct current data, and any equivalent variation or replacement shall fall within the scope of the embodiments.

S305: Determine a component signal of the red light alternating current signal based on the at least two red light alternating current signals; and determine a component signal of the infrared alternating current signal based on the at least two infrared alternating current signals.

In an example, a plurality of component signals in the plurality of red light alternating current signals are separated by using the independent component analysis algorithm, to obtain the plurality of component signals of the red light alternating current signals, where the plurality of component signals of the red light alternating current signals include an arterial signal. In addition, a plurality of component signals of the plurality of infrared alternating current signals are separated by using the independent component analysis algorithm, to obtain the plurality of component signals of the infrared alternating current signals, where the plurality of component signals of the infrared alternating current signals include an arterial signal. The plurality of component signals are independent of each other. In other words, the plurality of component signals are irrelevant to each other. In an example, n may be set to a quantity of red light alternating current signals, where n is greater than or equal to 1, and m is set to a quantity of component signals of the red light alternating current signals, where m is greater than or equal to 1. In an embodiment, if n=m, it means that a quantity of red light alternating current signals is equal to a quantity of component signals separated from the red light alternating current signals. The component signals include an arterial signal. Similarly, component signals of the plurality of infrared alternating current signals may be determined. In another example, a plurality of component signals in the plurality of red light/infrared alternating current signals may be separated by using a principal component analysis algorithm, to obtain the plurality of component signals of the red light/infrared alternating current signals. A person of ordinary skill in the art should note that, for a method for separating a plurality of component signals from a plurality of alternating current signals, any other equivalent variation or replacement that can be figured out shall fall within the scope of the embodiments.

S306: Determine red light alternating current data based on the component signal of the red light alternating current signal and a green light signal obtained after filtering processing, and determine infrared alternating current data based on the component signal of the infrared alternating current signal and the green light signal obtained after the filtering processing.

In an example, pre-processing of filtering and denoising is performed on the collected green light signal. Then, a green light signal obtained after the denoising is used as reference data of a pulse signal. The pulse signal is selected from the plurality of determined component signals of the red light alternating current signals, and the pulse signal is used as the red light alternating current data. In an example, linear correlation may be used to determine a correlation degree between the plurality of component signals of the red light alternating current signals and the green light signal obtained after the filtering processing. The correlation degree may be understood as a similarity degree. Then, a component signal that is of a red light alternating current signal and that is most closely correlated with the green light signal obtained after the filtering processing is determined as the red light alternating current data. Likewise, a component signal that is of an infrared alternating current signal and that is most closely correlated with the green light signal obtained after the filtering processing is determined as the infrared alternating current data.

S307: Determine pulse blood oxygen based on the red light direct current data, the red light alternating current data, the infrared direct current data, and the infrared alternating current data.

In an example, after the red light direct current data, the red light alternating current data, the infrared direct current data, and the infrared alternating current data are determined, the pulse blood oxygen may be determined according to a formula $$R = \frac{\frac{Red_{ac}}{Red_{dc}}}{\frac{IR_{ac}}{IR_{dc}}}.$$

A value of R represents a concentration proportional relationship between Hb and HbO2 in blood, $Red_{ac}$ is the red light alternating current data, $Red_{dc}$ is the red light direct current data, $IR_{ac}$ is the infrared alternating current data, and $IR_{dc}$ is the infrared direct current data.

S308: Query a pre-configured comparison table based on the pulse blood oxygen to determine blood oxygen saturation.

An SpO2 value corresponding to a pulse blood oxygen value is queried based on the pre-configured comparison table of pulse blood oxygen and SpO2.

In the embodiments, more information is collected by using a plurality of measurement points, then collected alternating current information is separated by using the independent component analysis algorithm, and denoising is performed by using the green light signal, so that interference caused by venous blood flows, capillaries, and the like can be eliminated, a disadvantage of a low signal-to-noise ratio is made up, and accuracy of a blood oxygen measurement on a wrist is increased.

Figure 4:
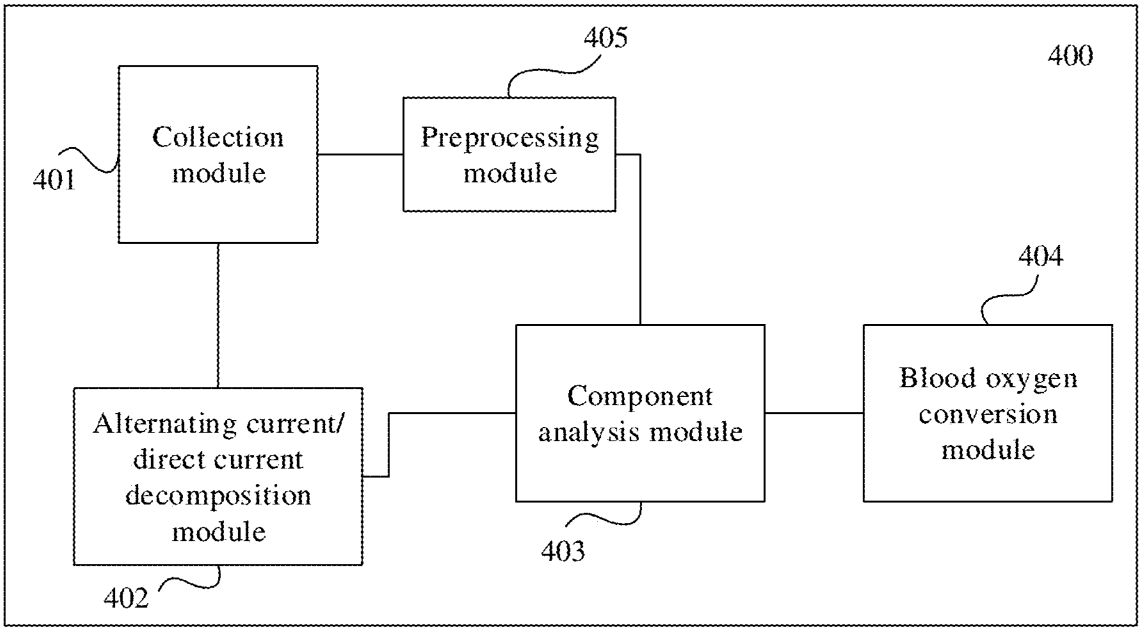
FIG. 4 is a schematic diagram of a blood oxygen detection apparatus according to an embodiment.

FIG. 4 is a schematic diagram of a blood oxygen detection apparatus according to an embodiment.

As shown in FIG. 4, a blood oxygen detection apparatus 400 is provided. The apparatus 400 includes: a collection module 401, configured to obtain at least two red light signals, at least two infrared signals, and a green light signal; an alternating current/direct current decomposition module 402, configured to: determine red light direct current data and a component signal of a red light alternating current signal based on the at least two red light signals, and determine infrared direct current data and a component signal of an infrared alternating current signal based on the at least two infrared signals, where the component signal includes an arterial signal; a component analysis module 403, configured to: determine red light alternating current data based on the component signal of the red light alternating current signal and the green light signal, and determine infrared alternating current data based on the component signal of the infrared alternating current signal and the green light signal; and a blood oxygen conversion module 404, configured to determine blood oxygen saturation based on the red light direct current data, the red light alternating current data, the infrared direct current data, and the infrared alternating current data.

In a possible implementation, the alternating current/direct current decomposition module 402 is further configured to: determine at least two red light direct current signals and at least two red light alternating current signals based on the at least two red light signals; determine the red light direct current data based on the at least two red light direct current signals; determine at least two infrared direct current signals and at least two infrared alternating current signals based on the at least two infrared signals; determine the infrared direct current data based on the at least two infrared direct current signals; determine the component signal of the red light alternating current signal based on the at least two red light alternating current signals; and determine the component signal of the infrared alternating current signal based on the at least two infrared alternating current signals. In another example, a red light direct current component and an infrared direct current component may alternatively be determined in another independent module.

In a possible implementation, the component analysis module 403 is further configured to: separate at least one component signal of the at least two red light alternating current signals by using an independent component analysis algorithm or a principal component analysis algorithm, to obtain at least one component signal of the red light alternating current signal, where the at least one component signal of the red light alternating current signal includes an arterial signal; and separate at least one component signal of the at least two infrared alternating current signals by using the independent component analysis algorithm or the principal component analysis algorithm, to obtain at least one component signal of the infrared alternating current signal, where the at least one component signal of the infrared alternating current signal includes an arterial signal.

In a possible implementation, the apparatus 400 further includes a preprocessing module 405. The preprocessing module 405 is configured to perform filtering processing on the green light signal. In an example, the preprocessing module may perform filtering processing on the green light signal by using a filter. A person of ordinary skill in the art should note that the filter is merely a possible implementation, and any equivalent replacement falls within the scope of the embodiments. A specific filter to be used is not limited herein. The component analysis module 403 is further configured to: determine the red light alternating current data based on the component signal of the red light alternating current signal and the green light signal obtained after the filtering processing, and determine the infrared alternating current data based on the component signal of the infrared alternating current signal and the green light signal obtained after the filtering processing.

In a possible implementation, the component analysis module 403 is further configured to: perform comparison based on the at least one component signal of the red light alternating current signal and the green light signal, and determine that data corresponding to at least one component signal, of the red light alternating current signal, closest to the green light signal is the red light alternating current data; and perform comparison based on the at least one component signal of the infrared alternating current signal and the green light signal, and determine that data corresponding to at least one component signal, of the infrared alternating current signal, closest to the green light signal is the infrared alternating current data.

In a possible implementation, the red light direct current data is an average value, a maximum value, a minimum value, or a median of the at least two red light direct current signals; and the infrared direct current data is an average value, a maximum value, a minimum value, or a median of the at least two infrared direct current signals.

In a possible implementation, the blood oxygen conversion module 404 is further configured to: determine pulse blood oxygen based on the red light direct current data, the red light alternating current data, the infrared direct current data, and the infrared alternating current data; and query a pre-configured comparison table based on the pulse blood oxygen, to determine the blood oxygen saturation.

In the embodiments, more information is collected by using a plurality of measurement points, then collected alternating current information is separated by using the independent component analysis algorithm, and denoising is performed by using the green light signal, so that interference caused by venous blood flows, capillaries, and the like can be eliminated, a disadvantage of a low signal-to-noise ratio is made up, and accuracy of a blood oxygen measurement on a wrist is increased.

Figure 5:
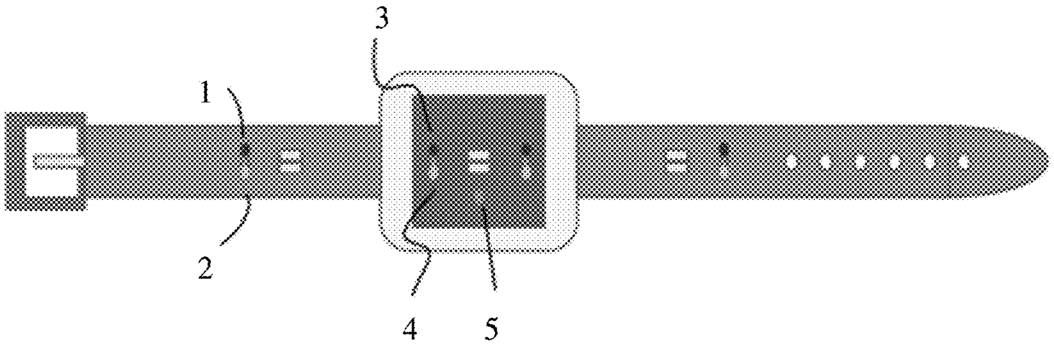
FIG. 5 is a schematic diagram of another blood oxygen detection apparatus according to an embodiment.

FIG. 5 is a schematic diagram of another blood oxygen detection apparatus according to an embodiment.

As shown in FIG. 5, a blood oxygen detection apparatus is provided. The apparatus includes at least two red light sensors, at least two infrared sensors, a green light sensor, and a processor. The at least two red light sensors are configured to obtain at least two red light signals, the at least two infrared sensors are configured to obtain at least two infrared signals, and the green light sensor is configured to obtain a green light signal. The processor is configured to: determine red light direct current data and a component signal of a red light alternating current signal based on the at least two red light signals; and determine infrared direct current data and a component signal of an infrared alternating current signal based on the at least two infrared signals. The component signal includes an arterial signal. The processor is further configured to: determine red light alternating current data based on the component signal of the red light alternating current signal and the green light signal; and determine infrared alternating current data based on the component signal of the infrared alternating current signal and the green light signal. The processor is further configured to determine blood oxygen saturation based on the red light direct current data, the red light alternating current data, the infrared direct current data, and the infrared alternating current data.

In an example, the processor is further configured to: determine at least two red light direct current signals and at least two red light alternating current signals based on the at least two red light signals; determine the red light direct current data based on the at least two red light direct current signals; determine at least two infrared direct current signals and at least two infrared alternating current signals based on the at least two infrared signals; determine the infrared direct current data based on the at least two infrared direct current signals; determine the component signal of the red light alternating current signal based on the at least two red light alternating current signals; and determine the component signal of the infrared alternating current signal based on the at least two infrared alternating current signals.

In an example, the processor is further configured to: separate at least one component signal of the at least two red light alternating current signals by using an independent component analysis algorithm or a principal component analysis algorithm, to obtain at least one component signal of the red light alternating current signal, where the at least one component signal of the red light alternating current signal includes an arterial signal; and separate at least one component signal of the at least two infrared alternating current signals by using the independent component analysis algorithm or the principal component analysis algorithm, to obtain at least one component signal of the infrared alternating current signal, where the at least one component signal of the infrared alternating current signal includes an arterial signal.

In an example, the processor is further configured to: perform filtering processing on the green light signal; determine the red light alternating current data based on the component signal of the red light alternating current signal and a green light signal obtained after the filtering processing; and determine the infrared alternating current data based on the component signal of the infrared alternating current signal and the green light signal obtained after the filtering processing.

In an example, the processor is further configured to: perform comparison based on the at least one component signal of the red light alternating current signal and the green light signal, and determine that data corresponding to at least one component signal, of a red light alternating current signal, closest to the green light signal is the red light alternating current data; and perform comparison based on the at least one component signal of the infrared alternating current signal and the green light signal, and determine that data corresponding to at least one component signal, of an infrared alternating current signal, closest to the green light signal is the infrared alternating current data.

In an example, the red light direct current data is an average value, a maximum value, a minimum value, or a median of the at least two red light direct current signals. The infrared direct current data is an average value, a maximum value, a minimum value, or a median of the at least two infrared direct current signals.

In an example, the processor is further configured to: determine pulse blood oxygen based on the red light direct current data, the red light alternating current data, the infrared direct current data, and the infrared alternating current data; and query a pre-configured comparison table based on the pulse blood oxygen, to determine the blood oxygen saturation.

In an example, the apparatus is a wearable intelligent device, and includes a watchband and an intelligent wearable device body. At least one red light sensor and at least one infrared sensor are disposed on the watchband. At least one red light sensor, at least one infrared sensor, and a processor are disposed on the intelligent wearable device body. A green light sensor is disposed on the watchband or the intelligent wearable device body.

In an example, at least two detection points are disposed on the blood oxygen detection apparatus. A red light sensor and an infrared sensor are disposed at each detection point. Arteries at a wrist are mostly distributed in a deep part of a human body, while veins are distributed near a surface of skin. A signal measured on the back of the wrist contains more venous compositions. On both sides of the wrist, arteries near ulna styloid process and radial styloid process are slightly near the skin, and data from these two positions contains less venous compositions. As shown in FIG. 5, the blood oxygen detection apparatus may be in a form of a smart watch, and two detection points ½ and ¾ may be disposed on the smart watch. The detection points ¾ may be disposed on a back of a watch face of the smart watch. When the smart watch is worn, the detection point ¾ is disposed on a back of a wrist of a user. The detection point ½ may be located within a 1 cm range of the ulna styloid process or radial styloid process. In other words, the detection point ½ may be disposed on the watchband. 1 and 3 are red light sensors, and 2 and 4 are infrared sensors. In addition, the apparatus is further provided with a photoplethysmography (photo plethysmography, PPG) sensor, namely, the foregoing green light sensor, which is marked as 5 in FIG. 5.

A person of ordinary skill in the art should note that a location of the detection point may be any location on the device. FIG. 5 is merely an optional implementation, and any equivalent replacement falls within the scope of the embodiments. A specific location of the detection point is not limited herein. A person of ordinary skill in the art should further note that the red light sensor and the infrared sensor at the detection point may be separated, or may be integrated together. A person of ordinary skill in the art should further note that a location of the PPG sensor used to detect green light may also be any location on the device. FIG. 5 is merely an optional implementation, and any equivalent replacement falls within the scope of the embodiments. A specific location of the PPG sensor is not limited herein.

In the embodiments, more information is collected by using the plurality of measurement points, then a plurality of component signals are separated from collected alternating current information by using the independent component analysis algorithm or the principal component analysis algorithm, and denoising is performed by using the green light signal, so that interference caused by venous blood flows, capillaries, and the like can be eliminated, a disadvantage of a low signal-to-noise ratio can be made up and accuracy of a blood oxygen measurement on the wrist is increased.

An ordinary person in the art may be further aware that, in combination with the examples described in the embodiments, units and algorithm steps may be implemented by electronic hardware, computer software, or a combination thereof. To clearly describe the interchangeability between the hardware and the software, the foregoing has generally described compositions and steps of each example according to functions. Whether the functions are performed by hardware or software depends on particular applications and design constraint conditions of the solutions. A person of ordinary skill in the art may use different methods to implement the described functions for each particular application, but it should not be considered that the implementation goes beyond the scope of the embodiments.

Persons of ordinary skill in the art may understand that all or some of the steps in each of the foregoing method of the embodiments may be implemented by a program instructing a processor. The foregoing program may be stored in a computer-readable storage medium. The storage medium may be a non-transitory medium, for example may be a random-access memory, read-only memory, a flash memory, a hard disk, a solid state drive, a magnetic tape, a floppy disk, an optical disc, or any combination thereof.

What is claimed is:

1. A method comprising:

radiating at least two red light signals, at least two infrared signals, and a green light signal into human tissue, wherein the at least two red light signals and the at least two infrared light signals are radiated into the human tissue at the same time;

measuring the at least two red light signals using at least two red light sensors, measuring the at least two infrared signals using at least two infrared sensors, and measuring the green light signal using a green light sensor;

obtaining, with a processor coupled to each of the at least two red light sensors, the at least two infrared sensors, and the green light sensor, the at least two red light signals from the at least two red light sensors;

obtaining, with the processor, the at least two infrared signals from the at least two infrared sensors;

obtaining, with the processor, the green light signal from the green light sensor;

decomposing, with the processor, the at least two red light signals into red light direct current data and a first component signal, wherein the red light direct current data reflects a status of deoxyhemoglobin in a venous blood vessel;

decomposing, with the processor, the at least two infrared signals into infrared direct current data and a second component signal, wherein the second component signal comprises an arterial signal;

determining, with the processor, red light alternating current data by correlating the first component signal with the green light signal;

determining, with the processor, infrared alternating current data by correlating the second component signal with the green light signal; and determining, with the processor, blood oxygen saturation based on the red light direct current data, the red light alternating current data, the infrared direct current data, and the infrared alternating current data, wherein at least one red light sensor of the at least two red light sensors and at least one infrared sensor of the at least two infrared sensors are disposed on a watchband, at least one red light sensor of the at least two red light sensors, at least one infrared sensor of the at least two infrared sensors, and the processor are disposed on an intelligent wearable device body, and the green light sensor is disposed either on the watchband or the intelligent wearable device body.

2. The method according to claim 1, wherein the decomposing of the at least two red light signals comprises:

determining a plurality of red light direct current signals and a plurality of red light alternating current signals based on the at least two red light signals, determining the red light direct current data based on the plurality of red light direct current signals, and determining the first component signal based on the plurality of red light alternating current signals, and wherein the decomposing of the at least two infrared signals comprises:

determining a plurality of infrared direct current signals and a plurality of infrared alternating current signals based on the at least two infrared signals, determining the infrared direct current data based on the plurality of infrared direct current signals, and determining the second component signal based on the plurality of infrared alternating current signals.

3. The method according to claim 2, wherein the determining of the first component signal comprises:

separating, from the plurality of red light alternating current signals, a red light component signal by using an independent component analysis algorithm or a principal component analysis algorithm to obtain the red light component signal, wherein the plurality of red light alternating current signals comprises at least one arterial signal of the red light signals; and wherein the determining of the second component signal comprises:

separating, from the plurality of infrared alternating current signals, an infrared component signal by using the independent component analysis algorithm or the principal component analysis algorithm to obtain the infrared component signal, wherein the plurality of infrared alternating current signals comprises at least one arterial signal of the infrared signals.

4. The method according to claim 3, wherein the determining of the red light alternating current data comprises:

comparing the red light component signal and the green light signal, and determining that data corresponding to the red light component signal closest to the green light signal is the red light alternating current data; and wherein the determining of the infrared alternating current data comprises:

comparing the infrared component signal and the green light signal, and determining that data corresponding to the infrared component signal closest to the green light signal is the infrared alternating current data.

5. The method according to claim 2, wherein the red light direct current data is an average value, a maximum value, a minimum value, or a median of the plurality of red light direct current signals; and the infrared direct current data is an average value, a maximum value, a minimum value, or a median of the plurality of infrared direct current signals.

6. The method according to claim 1, further comprising:

performing filtering processing on the green light signal, wherein the determining of the red light alternating current data comprises determining the red light alternating current data based on the first component signal and a filtered green light signal obtained after the filtering processing; and wherein the determining of the infrared alternating current data comprises determining the infrared alternating current data based on the second component signal and the filtered green light signal obtained after the filtering processing.

7. The method according to claim 1, wherein the determining blood oxygen saturation comprises:

determining pulse blood oxygen based on the red light direct current data, the red light alternating current data, the infrared direct current data, and the infrared alternating current data; and querying a pre-configured comparison table based on the pulse blood oxygen to determine the blood oxygen saturation.

8. An apparatus comprising:

at least two red light sensors configured to obtain at least two red light signals;

at least two infrared sensors configured to obtain at least two infrared signals, wherein the at least two red light signals and the at least two infrared signals are radiated into human tissue at the same time;

a green light sensor configured to obtain a green light signal; and a processor operatively connected to the at least two red light sensors, the at least two infrared sensors, and the green light sensor, the processor configured to:

decompose the at least two red light signals into red light direct current data and a first component signal, wherein the red light direct current reflects a status of deoxyhemoglobin in a venous blood vessel;

decompose the at least two infrared signals into infrared direct current data and a second component signal, wherein the second component signal comprises an arterial signal;

determine red light alternating current data by correlating the first component signal with the green light signal;

determine infrared alternating current data by correlating the second component signal with the green light signal; and determine blood oxygen saturation based on the red light direct current data, the red light alternating current data, the infrared direct current data, and the infrared alternating current data, wherein at least one red light sensor of the at least two red light sensors and at least one infrared sensor of the at least two infrared sensors are disposed on a watchband, at least one red light sensor of the at least two red light sensors, at least one infrared sensor of the at least two infrared sensors, and the processor are disposed on an intelligent wearable device body, and the green light sensor is disposed either on the watchband or the intelligent wearable device body.

9. The apparatus according to claim 8, wherein the processor is further configured to:

determine a plurality of red light direct current signals and a plurality of red light alternating current signals based on the at least two red light signals;

determine the red light direct current data based on the plurality of red light direct current signals;

determine a plurality of infrared direct current signals and a plurality of infrared alternating current signals based on the at least two infrared signals;

determine the infrared direct current data based on the plurality of infrared direct current signals;

determine the first component signal based on the plurality of red light alternating current signals; and determine the second component signal based on the plurality of infrared alternating current signals.

10. The apparatus according to claim 9, wherein the processor is further configured to:

separate, from the plurality of red light alternating current signals, a red light component signal by using an independent component analysis algorithm or a principal component analysis algorithm, to obtain the red light component signal, wherein the plurality of red light alternating current signals comprises at least one arterial signal of the red light signals; and separate, from the plurality of infrared alternating current signals, an infrared component signal by using the independent component analysis algorithm or the principal component analysis algorithm, to obtain the infrared component signal, wherein the plurality of infrared alternating current signals comprises at least one arterial signal of the infrared signals.

11. The apparatus according to claim 10, wherein the processor is further configured to:

compare the red light component signal and the green light signal;

determine, in performing the determination of the red light alternating current data, that data corresponding to the red light component signal, based upon the comparison of the red light component signal and the green light signal, is the red light alternating current data;

compare the infrared component signal and the green light signal; and determine, in performing the determination of the infrared alternating current data, that data corresponding to the infrared component signal, based upon the comparison of the infrared component signal and the green light signal, is the infrared alternating current data.

12. The apparatus according to claim 9, wherein the red light direct current data is an average value, a maximum value, a minimum value, or a median of the plurality of red light direct current signals; and the infrared direct current data is an average value, a maximum value, a minimum value, or a median of the plurality of infrared direct current signals.

13. The apparatus according to claim 8, wherein the processor is further configured to:

perform filtering processing on the green light signal;

determine the red light alternating current data based on the first component signal and a filtered green light signal obtained after the filtering processing; and determine the infrared alternating current data based on the second component signal and the filtered green light signal obtained after the filtering processing.

14. The apparatus according to claim 8, wherein the processor is further configured to:

determine pulse blood oxygen based on the red light direct current data, the red light alternating current data, the infrared direct current data, and the infrared alternating current data; and query a pre-configured comparison table based on the pulse blood oxygen to determine the blood oxygen saturation.

* * * * *